US 6,509,006 B1
Jan. 21, 2003

(12) United States Patent
Platz et al.

(54) DEVICES COMPOSITIONS AND METHODS FOR THE PULMONARY DELIVERY OF AEROSOLIZED MEDICAMENTS

(75) Inventors: Robert M. Platz, Half Moon Bay, CA (US); John S. Patton, San Carlos, CA (US); Linda Foster, Sunnyvale, CA (US); Mohammed Eljamal, San Jose, CA (US)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

(21) Appl. No.: 09/427,075

(22) Filed: Oct. 26, 1999

Related U.S. Application Data

(63) Continuation-in-part of application No. 08/417,507, filed on Apr. 4, 1995, now abandoned, and a continuation of application No. 08/383,475, filed on Feb. 1, 1995, and a continuation of application No. 08/313,707, filed on Sep. 27, 1994, and a continuation of application No. 08/309,691, filed on Sep. 21, 1994, and a continuation of application No. 08/246,034, filed on May 18, 1994, and a continuation of application No. 08/232,849, filed on Apr. 25, 1994, and a continuation of application No. 08/044,358, filed on Apr. 7, 1993, and a continuation-in-part of application No. 07/910,048, filed on Jul. 8, 1992.

(51) Int. Cl.$^7$ .............................. A61K 9/12; A61K 9/14
(52) U.S. Cl. ............................. 424/46; 424/45; 424/489
(58) Field of Search ............................. 424/45, 46, 489

(56) References Cited

U.S. PATENT DOCUMENTS

| | | |
|---|---|---|
| 2,598,525 A | 5/1952 | Fox |
| 3,202,731 A | 8/1965 | Grevenstuk et al. |
| 3,300,474 A | 1/1967 | Flodin et al. |
| 3,314,803 A | 4/1967 | Tarrytown et al. |
| 3,362,405 A | 1/1968 | Hazel |
| 3,425,600 A | 2/1969 | Abplanalp |
| 3,540,927 A | 11/1970 | Niimi et al. |
| 3,554,768 A | 1/1971 | Feldman |
| 3,608,066 A | 9/1971 | Illartein |
| 3,620,776 A | 11/1971 | Mishkin et al. |
| 3,666,496 A | 5/1972 | Honey et al. |
| 3,674,901 A | 7/1972 | Shepherd et al. |
| 3,764,716 A | 10/1973 | Rainwater et al. |
| 3,921,637 A | 11/1975 | Bennie et al. |
| 3,964,483 A | 6/1976 | Mathes |
| 3,971,852 A | 7/1976 | Brenner et al. |
| 3,991,304 A | 11/1976 | Hillsman |
| 3,991,761 A | 11/1976 | Cocozza |
| 3,994,421 A | 11/1976 | Hansen |
| 4,036,223 A | 7/1977 | Obert |
| 4,069,819 A | 1/1978 | Valentini et al. |
| 4,098,273 A | 7/1978 | Glenn |
| 4,109,019 A | 8/1978 | Moore |
| 4,153,689 A | 5/1979 | Hiral et al. |
| 4,206,200 A | 6/1980 | Guthöhrlein et al. |
| 4,249,526 A | 2/1981 | Dean et al. |
| 4,253,468 A | 3/1981 | Lehmbeck |
| 4,294,624 A | 10/1981 | Veltman |
| 4,294,829 A | 10/1981 | Suzuki et al. |
| 4,338,931 A | 7/1982 | Cavazza |
| 4,423,079 A | 12/1983 | Kline |
| 4,446,862 A | 5/1984 | Baum et al. |
| 4,452,239 A | 6/1984 | Malem |
| 4,484,577 A | 11/1984 | Sackner et al. |
| 4,503,035 A | 3/1985 | Pestka et al. |
| 4,533,552 A | 8/1985 | Kawamata et al. |
| 4,534,343 A | 8/1985 | Nowacki et al. |

(List continued on next page.)

FOREIGN PATENT DOCUMENTS

| | | |
|---|---|---|
| BE | 902 257 | 8/1985 |
| DE | 18 12 574 | 6/1970 |
| DE | 24 15 159 | 10/1975 |
| DE | 31 41 498 | 4/1983 |
| DE | 01 61 072 | 9/1984 |
| EP | 0 015 123 | 9/1980 |

(List continued on next page.)

OTHER PUBLICATIONS

US 5,849,884, 12/1998, Wolszwillo et al. (withdrawn)

J. Hanes et al. (1997). Proc. Int'l Symp. Control Rel. Bioactive Matter 24:57–58.*

Andrew, Edmund L., "Gelatin Capsules Revamped For New Generation Of Pills," *New York Times*, Saturday, Sep. 16, 1992, 19 (N), 35 (L), col 5, 9 col in.

Annear, D. I., "Observations on Drying Bacteria From the Forzen and From the Liquid State," *Austral. J. Exp. Biol.*, vol. 36, pp. 211–221.

(List continued on next page.)

*Primary Examiner*—Jose' G. Dees
*Assistant Examiner*—Mina Haghighatian
(74) *Attorney, Agent, or Firm*—Burns Doane Swecker & Mathis LLP

(57) ABSTRACT

According to the subject invention, dispersible dry powder pharmaceutical-based compositions are provided, including methods for their manufacture and dry powder dispersion devices. A dispersible dry powder pharmaceutical-based composition is one having a moisture content of less than about 10% by weight (% w) water, usually below about 5% w and preferably less than about 3% w; a particle size of about 1.0–5.0 $\mu$m mass median diameter (MMD), usually 1.0–4.0 $\mu$m MMD, and preferably 1.0–3.0 $\mu$m MMD; a delivered dose of about >30%, usually >40%, preferably >50%, and most preferred >60%; and an aerosol particle size distribution of about 1.0–5.0 $\mu$m mass median aerodynamic diameter (MMAD), usually 1.5–4.5 $\mu$m MMAD, and preferably 1.5–4.0 MMAD. Such composition are of pharmaceutical grade purity.

2 Claims, No Drawings

U.S. PATENT DOCUMENTS

| | | |
|---|---|---|
| 4,559,298 A | 12/1985 | Fahy |
| 4,590,206 A | 5/1986 | Forrester et al. |
| 4,599,311 A | 7/1986 | Kawasaki |
| 4,617,272 A | 10/1986 | Kirkwood et al. |
| 4,624,251 A | 11/1986 | Miller |
| 4,627,432 A | 12/1986 | Newell et al. |
| 4,649,911 A | 3/1987 | Knight et al. |
| 4,677,975 A | 7/1987 | Edgar et al. |
| 4,698,328 A | 10/1987 | Neer et al. |
| 4,719,762 A | 1/1988 | Osabe |
| 4,739,754 A | 4/1988 | Shaner |
| 4,790,305 A | 12/1988 | Zoltan et al. |
| 4,806,343 A | 2/1989 | Carpenter et al. |
| 4,807,814 A | 2/1989 | Douche et al. |
| 4,811,731 A | 3/1989 | Newell et al. |
| 4,819,629 A | 4/1989 | Jonson |
| 4,820,534 A | 4/1989 | Saleeb et al. |
| 4,823,784 A | 4/1989 | Bordoni et al. |
| 4,824,938 A | 4/1989 | Koyama et al. |
| 4,830,858 A | 5/1989 | Payne et al. |
| 4,833,125 A | 5/1989 | Neer et al. |
| 4,855,157 A | 8/1989 | Tashiro et al |
| 4,857,319 A | 8/1989 | Crowe et al. |
| 4,876,241 A | 10/1989 | Feldman et al. |
| 4,884,565 A | 12/1989 | Cocozza |
| 4,889,114 A | 12/1989 | Kladders |
| 4,891,319 A | 1/1990 | Roser |
| 4,897,353 A | 1/1990 | Carpenter et al. |
| 4,907,583 A | 3/1990 | Wetterlin et al. |
| 4,919,962 A | 4/1990 | Arora et al. |
| 4,926,852 A | 5/1990 | Zoltan et al. |
| 4,927,763 A | 5/1990 | Sudoma et al. |
| 4,931,361 A | 6/1990 | Baldeschwieler et al. |
| 4,942,544 A | 7/1990 | McIntosh et al. |
| 4,956,295 A | 9/1990 | Sudoma |
| 4,968,607 A | 11/1990 | Dower et al. |
| 4,984,158 A | 1/1991 | Hillsman |
| 4,995,385 A | 2/1991 | Valentini et al. |
| 5,011,678 A | 4/1991 | Wang et al. |
| 5,017,372 A | 5/1991 | Hastings |
| 5,026,566 A | 6/1991 | Roser |
| 5,027,806 A | 7/1991 | Zoltan et al. |
| 5,033,463 A | 7/1991 | Cocozza |
| 5,035,237 A | 7/1991 | Newell et al. |
| 5,048,514 A | 9/1991 | Ramella |
| 5,049,388 A | 9/1991 | Knight et al. |
| 5,081,228 A | 1/1992 | Dower et al. |
| 5,093,316 A | 3/1992 | Lezdey et al. |
| 5,098,893 A | 3/1992 | Franks et al. |
| 5,099,833 A | 3/1992 | Michaels |
| 5,113,855 A | 5/1992 | Newhouse |
| 5,124,162 A | 6/1992 | Bošković et al. |
| 5,149,543 A | 9/1992 | Cohen et al. |
| 5,149,653 A | 9/1992 | Roser |
| 5,161,524 A | 11/1992 | Evans |
| 5,180,812 A | 1/1993 | Dower et al. |
| 5,186,164 A | 2/1993 | Raghuprasad |
| 5,192,528 A | 3/1993 | Radhakrishnan et al. |
| 5,200,399 A | 4/1993 | Wettlaufer et al. |
| 5,204,108 A | 4/1993 | Illum |
| 5,206,200 A | 4/1993 | Bush et al. |
| 5,230,884 A | 7/1993 | Evans et al. |
| 5,253,468 A | 10/1993 | Raymond |
| 5,254,330 A | 10/1993 | Ganderton et al. |
| 5,290,765 A | 3/1994 | Wettlaufer et al. |
| 5,295,479 A | 3/1994 | Lankinen |
| 5,302,581 A | 4/1994 | Sarin et al. |
| 5,309,900 A | 5/1994 | Knoch et al. |
| 5,320,094 A | 6/1994 | Laube et al. |
| 5,320,714 A | 6/1994 | Brendel |
| 5,331,953 A | 7/1994 | Andersson et al. |
| 5,354,562 A | 10/1994 | Platz et al. |
| 5,364,838 A | 11/1994 | Rubsamen |
| 5,376,359 A | 12/1994 | Johnson |
| 5,376,386 A | 12/1994 | Ganderton et al. |
| 5,466,701 A | 11/1995 | Hlasta |
| 5,488,062 A | 1/1996 | Dunlap et al. |
| 5,506,203 A | 4/1996 | Bäckström |
| 5,518,998 A | 5/1996 | Bäckström |
| 5,554,382 A | 9/1996 | Castor |
| 5,626,871 A | 5/1997 | Makino et al. |
| 5,707,644 A * | 1/1998 | Illum |
| 5,780,014 A | 7/1998 | Eljamal et al. |
| 5,855,913 A | 1/1999 | Hanes et al. |

FOREIGN PATENT DOCUMENTS

| | | |
|---|---|---|
| EP | 0 072 046 | 2/1983 |
| EP | 72046 * | 2/1983 |
| EP | 0 111 216 | 6/1984 |
| EP | 0 140 489 | 5/1985 |
| EP | 0 229 810 | 7/1987 |
| EP | 0 237 507 | 9/1987 |
| EP | 0 289 336 | 11/1988 |
| EP | 0 347 779 | 12/1989 |
| EP | 0 360 340 | 3/1990 |
| EP | 0 366 303 | 5/1990 |
| EP | 0 383 569 | 8/1990 |
| EP | 0 467 172 | 1/1992 |
| EP | 0 468 914 | 1/1992 |
| EP | 0 490 797 | 6/1992 |
| EP | 0 506 293 | 9/1992 |
| EP | 0 611 567 | 8/1994 |
| ES | 84-03520 | 2/1983 |
| FR | 2257351 | 8/1975 |
| GB | 1 288 094 | 9/1972 |
| GB | 1 477 775 | 6/1977 |
| GB | 1 527 605 | 10/1978 |
| GB | 2 105 189 | 3/1983 |
| GB | 2 126 588 | 3/1984 |
| JP | 59-095885 | 2/1984 |
| JP | 61.293.201 | 12/1986 |
| NL | 7712041 | 5/1979 |
| RU | 883174 | 11/1981 |
| SU | 0628930 | 9/1978 |
| SU | 1003926 | 3/1983 |
| WO | 86/04095 | 7/1986 |
| WO | 87/00196 | 1/1987 |
| WO | 87/05300 | 9/1987 |
| WO | 88/04556 | 6/1988 |
| WO | 88/09163 | 12/1988 |
| WO | 90/05182 | 5/1990 |
| WO | 90/07351 | 7/1990 |
| WO | 90/09780 | 9/1990 |
| WO | 90/15635 | 12/1990 |
| WO | 91/02545 | 3/1991 |
| WO | 91/02558 | 3/1991 |
| WO | 91/16038 | 10/1991 |
| WO | 91/16882 | 11/1991 |
| WO | 93/02712 | 2/1993 |
| WO | 93/09832 | 5/1993 |
| WO | 94/08552 | 4/1994 |
| WO | 95/00127 | 1/1995 |
| WO | 95/23613 | 9/1995 |
| WO | 96/09814 | 4/1996 |
| WO | 97/03649 | 2/1997 |
| ZA | 94/0155 | 1/1994 |

OTHER PUBLICATIONS

Bone, S. and Pethig R., "Dielectric Studies of Protein Hydration and Hydration Induced Flexibility," *J. Mol. Biol.*, 1985, vol. 181, pp. 323–326.

Bruni, Fabio and A. Carl Leopold, "Glass Transistions in Soybean Seed, Relevance to Anhydrous Biology," *Plant. Physiol.*, 1991, vol. 96, pp. 660–663.

Burke, Michael J., "The Glassy State and Survival of Anhydrous Biological Systems," *Membranes*, Metabolism and Dry Organisms, Appendix D, 1986, A. Carl Leopold Editor, pp. 358–363.

Caffrey Martin et al., "Lipid–Sugar Interactions, Relevance to Anhydrous Biology," *Plant. Physiol.*, 1988, vol. 86, pp. 754–758.

Carpenter, John F. et al., "Stabilization of Phosphofructokinase With Sugars During Freeze–Drying: Characterization Of Enhanced Protection in the Presence of Divalent Cations," *Biochimica et Biophysica Acta*, vol. 923, 1987, pp, 109–115.

Carpenter, John F. et al. "Stabilization of Phosphofructokinase During Air–Drying With Sugars and Sugar/Transition Metal Mixture," *Cryobiology*, 1987 vol. 24, pp. 455–464.

Carpenter, John F, et al., "Modes of Stabilization of a Protein by Organic Solutes During Desiccation," *Cryobiology*, 1988, vol. 25, pp. 459–470.

Chopin, A. et al., "Destruction de Microbacterium Lacticum, *Escherichia coli* et *Staphylococcus aureus* au cours du sechage du lait par atomisation," *Can. Microbiol.*, 1977, 23:716–720. No translation.

Colthorpe P. et al., "The Pharmacokinetics of Pulmonary–Delivered Insulin: A Comparison of Interatracheal and Aerosol Administration to the Rabbit," *Pharmaceutical Research*, 1992, vol. 9, No. 6, pp. 764–768.

Crowe, John H. et al., "Stabilization of Dry Phospholipid Bilayers and Proteins by Sugars," *Biochem. J.*, 1987, vol. 242, pp. 1–10.

Crowe, John H. et al., "Are Freezing and Dehydration Similar Stress Vectors? A comparison of Modes of Interaction of Stabilizing Solutes With Biomolecules," *Cryoboloby*, 1990, vol. 27, pp. 219–231.

Fahy, Gregory M., "The Relevance of Cryoprotectant 'Toxicity" to Cryobiology,' *Cryobiology*, 1986, vol. 23, pp. 1–13.

Finney, J. L. and P. L. Poole, "Protein Hydaration and Enzyme Activity: The Role of Hydration Induced Conformation and Dynamic Changes in the Activity of Lysozyme," *Comments Mol. Cell. Biophys.*, 1984, vol. 2 (3–4), pp. 129–151.

Flink, James M., Chapter 17 entitled "Structure and Structure Transisition in Dried Carbohydrate Materials," *Physical Propertiesof Foods*, 1983, M. Peleg and E.B. Bagley (Editions), pp. 473–521.

Gendler, Paul L. and Henry Rapoport, "Permethyk Analogue of the Pyrrolic Antibiotic Disctamycin A," *J. Med, Chen.*, 1981, vol. 24, No. 1, pp. 33–38.

Goetz, Philip W., Editor, Chapter Climate and Weather entitled "Atmospheric Humidity and Precipitation," *The New Encyclopedia Britannica*, vol. 16, Copyright 1985, pp. 476–479.

Green, J. L. and C. A. Angell, "Phase Relations and Vitrification in Saccharide–Water Solutions and The Trehalose Anomaly," *J. Phys. Chem.*, 1989, vol. 93, pp. 2880–2882.

Heinemann, L., et al., "Time–Action Profile of Inhaled Insulin," *Diabetic Medicine*, 1997, vol. 14, pp. 63–72.

Herrington, B. L., "Some Physico–Chemical Properties of Lactose: The Spontaneous Crystallization of Super–Saturated Solutions of Lactose," *J. Dairy Science*, 1934, vol. 17, pp. 501–518.

Iijima, Teiji and Takesiii Sakane, "A Method for Preservation of Bacteria and Bacteriophages by Drying in Vacuo," *Cryobiology*, 1973, vol. 10, pp. 379–385.

Josic, Djuro, "Optimization of Process Conditions for the Production of Active Dry Yeast," *Lebensm—Wiss, U. Technol.*, 1982, vol. 15, No. 1, pp. 5–14.

Karel, M., "Water Relations of Foods," *R. B. Duckworth*, Ed., 1975 Academic Press, NY, pp. 648–649.

Kauzmann, Walter, "The Nature of the Glassy State and The Behavior of Liquids at Low Temperatures," Department of Chemistry, Princeton University, Princetown, New Jersey, Received Mar. 1, 1948, pp. 219–227.

Kim, Suk Shin and Santi R. Bhowmik, "Survival of Lactic Acid Bacteria During Spray Drying of Plain Yogure," *Journal of Food Science*, vol. 55, No. 4, 1990, pp. 1008–1010, 1048.

Kohler, Dieter et al., "Night Radicaktives Verfahren zur Messung der Lungenpermeabilitat; Inhalation Von Insulin," *Atemu, Lungenkrkh, Jahrgang*, 1987, vol. 13, No. 6, pp. 230–232. For English Avstract see Schulter Reference.

Labuza, Theodore P. et al., Engineering Factors in Single––Cell Protein Production, II. Spray Drying and Cell Viability,: Biotechnology and Bioengineering, 1970, vol. XII, pp. 135–140.

Levine, Harry et al., "Principles of 'Cryostabilization' Technology From Structure/Property Relationships of Carbohydrate/Water Systems," *Cryo–letters*, 1988, vol. 9, pp. 21–63.

Levine Harry and Louise Slade, A Polymer Physico–Chemical Approach to the Study of Commercial Starch Hydrolysis Products (SHPs), *Carbohydrate Polymers*, 1986, vol. 6, pp. 213–244.

Malik, K. A. "A Simplified Liquid–Drying Method for the Preservation of Microorganism Sensitive to Freezing and Freeze–Drying," *Journal of Microbiological Methods*, 1990, vol. 12, pp. 125–132.

Metwally, M. M. et al., "Spray Drying of Lactic Acid Culture, I. The Effect of Spray Drying Conditions on the Survival of Microorganisms," *Egyptian J. Dairy Sci.*, 1989, vol. 17, pp. 35–43.

Metwally, M. M. et al., "Spray Drying of Lactic Acid Cultures, II. The Effect of Culture Conditions and Storage on Microorganisms Survival," *Egyptian J. Dairy Sci.*, 1989, vol. 17, pp. 273–275, 279.

Mumenthaler, Marco et al., "Feasibility Study on Spray–Drying Protein Pharmaceuticals: Recombinant Human Growth Hormone and Tissue–Type Plasminogen Activator," *Pharmaceutical Reseach*, 1994, vol. 11, No. 1, Plenum Publishing Corporation, pp. 12–20.

Peri, C. et al., "Thermodynamics of Water Sorption on *Sacc. cerevisiae* and Cell Viability During Spray–Drying," *Lebensm—Wiss. U. Technol.*, 1974, vol. 7, No. 2, pp. 76–81.

Pharmacia LKB Biotechnology Brochure entitled "A Cure For The Common Cold—Ready To Go DNA Labelling Kit Pre–Mixed Reactions That Store At Room Temperature," Undated, 9 pages.

Pikal, Michael et al., "Moisture Transfer From Stopper To Product And Resulting Stability Implications," *Developments in Biological Standardardization*, 1991, vol. 74, International Symposium on Biological Product Freeze–Drying and Formulation, pp. 165–179.

Poole, P. L. et al., "Sequential Hydration of a Dry Globular Protein," Biopolymer, 1983, vol. 22, pp. 255–260.

Poole, P. L. et al., "Hydration–induced Conformational and Flexibility Changes in Lysozyme at Low Water Contents," *Int. J. Biol. Macromol.*, Oct. 1983, vol. 5, pp. 308–310.

Prajapati, J. B. et al., "Survival of *Lacobacillus acidocphilus* in Blended—Spray Dried Acidophilus Preparations," *Australian Journal of Dairy Technology* Mar./Jun. 1987, pp. 17–21.

Roos, Y et al., "Effects of Glass Transitions on Dynamic Phenomena, Figure 10.8," *The Glassy State in Foods*, published by J. M. Blanchard and P. J. Lillford (Nillington University Press), 1993, one page.

Roser, Bruce, "Thelalose Drying: A Nobel Replacement For Freez–Drying," *Biopharm*, Sep. 1991, vol. 4, No. 8, pp. 47–53.

Schneider, Z. et al., "Thermostabilitiy of Enzyme in the Three–Dimensional Network of Polisaccharide Chains," *Bulletin de l'Academie Polonaise des Sciences*, 1968, CL. II, vol. XVI, No. 4, 1968, Serie des Sciences Biologiques, pp. 203–204.

Sciarra, Hohn J. et al., Chapter 93 entitled "Aerosols," *Remington's Pharmaceutical Sciences*, 17$^{th}$ Edition, 1985, Mack Publishing Company, Alfonso R. Gennaro (Editor), pp. 1622–1677.

Skrabanja, Arno et al., "Lyophilization of Biotechnology Products," *FDA Journal of Pharmceutical Science & Technology*, Nov.–Dec. 1994, vol. 48, No. 6, pp. 311–317.

Slade, Louise et al., "Structural Stability of Intermediate Moisture Foods—A New Understanding?" *Food Structure*, Its Creation and Evaluation, 1998, pp. 115–147.

Tertyshny, V.N. et al., "Effect of Orthophosphoric Acid on Survivability of Propionibacterium Shermanii After Spray Drying And In The Process of Storage," *Microbiology Journal*, 1988, vol. 50, No. 3, pp. 49–52, English Summary on p. 52.

Townsend, Michael et al., "Use of Lyoprotectants in The Freez–Drying of a Model Protein Rebonuclease A," *Journal of Parenteral Sciences & Technology*, Nov.–Dec. 1998, vol. 42, No. 6, pp. 190–199.

Tsourouflis, Spyros et al., "Loss of Structure in Freeze–Dried Carbohydrates Solutions: Effect of Temperature, Moisture Content and Composition," *J. Sci, Fd Agric.*, 1976, vol. 27, pp. 509–519.

Uedaira, Hatsuho et al., "The Effect of Sugars On The Thermal Denturation of Lysozyme," *Bulletin of The Chemical Society of Japan*, Sep. 1980, vol. 53, pp. 2451–2455.

Van de Bek, M. J. et al., "Preservation of the Enzymatic Activity of Rennin During Spray Drying And During storage, And The Effect of Sugars And Certain Other Activities," *Neth. Milk Dairy J.*, 1969, vol. 23, pp. 46–54.

Wettlaufer, Scott H. et al., "Revelance of Amodori And Maillard Products To Seed Deterioration," *Plant Physiol.*, Apr. 1991, vol. 97, pp. 165–169.

White, G. W. et al., "The Glassy State in Certain Sugar–Containing Food Products," *J. Food TEchnol.*, 1966, vol. 1, pp. 73–92.

Williams, Adeyinka et al., "Vial Breakage by Frozen Mannitol Solutions: Correlation With Thermal Characteristics And Effect of Stereoigomerism, Additives, and Vial Configuration," *Journal of Parenteral Science & Technology*, Mar.–Apr. 1991, vol. 45, No. 2, pp. 94–100.

Williams, Roberts J. et al., "The Glassy State in Corn Embryos," *Plant Physiol.* 1989, vol. 89, p. 977–981.

Yoshida, H., "Absortion of Insulin Delivered to Rabbit Trachea Using Aerosol Dosage Form," *Journal of Pharmaceutical Sciences*, May 1979, vol. 68, No. 5, pp. 670–671.

Abstract—Japanese Patents Gazette—Week 8604—Apr. 12, 1985, Section Chemical JP 60244288–A, Applicant: Okura Seiyaku KK, one page, and translation in English.

Abstract—Japanese Patents Gazette—Week 8746—Jul. 10, 1987, Section Chemical JP 62228272–A, Applicant: Amano Pharm, KK,, one page.

Abstract—Japanese Patents Gazette—Week 8750—Section Chemical JP 62255434–A Fuji Seiyu KK—Nov. 7, 1987— Enventors: Tagawa Kunio and Kurosawa Wahei—Applicant: Fuji Oil Co Ltd.

Abstracts, 18$^{th}$ Annual Meeting, Cryobiology, vol. 18, No. 6, Dec. 1981, see Nos. 20 p. 617 & 24 p. 618, Author Gregory Fahy.

Health News Daily, Friday, Jan. 20, 1995, vol. 7, No. 13, one page.

"Clean–Up With Pulsed Jets, "*Manufacturing Chmist*, Apr. 1992, pp. 29, 31.

"Production of Trehalose Dried Eggs, " D5, Tg Measurements, Undated, 10 pages.

Drytec, Compact Laboratory Dryer, Undated Brochure, one page.

Lab–Plant Ltd., Sd–04 Laboratory Scale Spray Drier, Undated Brochure, 4 pages.

E. Bjork, "Degradable Starch Microspheres as a Nasal Deliver Systwem For Insulin," Int'l. J. of Pharmaceuticals, vol. 47, (1998), pp. 233–238.

M. Bohnet, "Calculation and Design of Gas/Solid–Injectors," Powder Technology, pp. 302–313 (1984).

G.K. Budrik et al., "Ejector Feeders for pneumatic Transport Systems," Chemical and Petroleum Engineering, vol. 14, Nos. 9–10, Sep.–Oct. 1978.

P.R. Byron et al., "Drug Delivery via the Respiratory Tract," J. of Aerosol Medicine, vol. 7, No. 1 (1994), pp. 49–75.

Y. W. Chien et al., "Intranasal Drug Delivery for Systemic Medicaitons," CRC Critical Reviews in Therapuetic Drug Carries Systems, vol. 4, Issue 2 (1987), pp. 67–92.

P. Colthorpe et al., "The Pharmacokinetics of Pulmonary–Delived Insulin: A Comparison of interatracheal and Aerosol Administration to the Rabbit," Pharmaceutical Research, vol. 9, No. 6, 1992, pp. 764–768.

Guus S.M.J.E. Dutchateau et al., "Bile Salts and intranasal Drug Absorption," Int'l. J. Of Pharmaceuticals, vol. 31, (1986), pp. 193–199.

R.B. Elliott et al., "Paraenteral Absorption of Insulin from the Lung in Diabetic Children," Aust. Paediatr. J. (1987) vol. 23, 293–297.

L.S. Fox et al., "Performance of a Venturi Educator as a Feeder in a Pneumatic Conveying System," Powder and Bulk Engineering, Mar. 1988, pp. 33–36.

T. Friedman., "Progress Toward Human Gene Therpay," *Science*, vol. 244, Jun. 16, 1989, pp. 1275–1281.

M. Gansslen, "Uber Inhalation von Insulin," *Klin. Wochenschr.*, 1925, vol. 4, No. 71 (without translation).

J.F. Habener et al., "Parathyriod Hormone: Secretion and Metabolism In Vivo," *Proc. Nat. Acad. Sci. USA*, vol. 68, No. 12, pp. 2986–2991, Dec. 1971.

R. H. Hastings, "Clearance of Different–Sized Proteins from the Alveolar Space in Humans and Rabbits," *The American Physiological Society*, 1992, pp. 1310–1316.

R.D. Hesch et al., "Pulsatile Secrettion of Parathyroid Hormone and its Action on a Type I and Type II PTH Receptor: A Hypothesis for Understanding Osteoporosis," *Calcified Tissue International*, (1988), vol. 42, pp. 341–344.

B.L. Laube et al., "Preliminary Study of the Efficacy of Insulin Aerosol Delivered by Oral Inhalation in Diabetic Patients," *JAMA*, vol. 269, No. 16, Apr. 28, 1993, pp. 2106–2109.

S.W. Lee et al., Development of an Aerosol Dosage Form Containing Insulin,: Reprinted from *J. of Pharmaceutical Sciences*, vol. 65, No. 4, 1976, pp. 567–572.

F. Liu et al., "Pulmonary Delivery of Free and Liposomal Insulin," *Pharmaceutical Research*, vol. 10, No. 2, 1993, pp. 228–232.

M. Nagano et al., "New Method of Insulin Therapy: Transpulmonary Absorption of Insulin," *Jikeikai Med. J.*, vol. 32, No. 3, (1985), pp. 503–506.

T. Nagai et al., "Powder Dosage Form of Insulin for Nasal Administration," J. of Controlled Release, vol. 1, (1984), pp. 15–22.

R.M. Neer et al., The Use of Parathyroid Hormone Plus 1,25–Dihydroxyvitamin D to Increase Trabecular Bone in Osteoporotic Men and Postmenopausal Women, *Osteoporosis*, (1987), pp. 829–835.

M.M. Nieminen et al., "Aerosol Deposition in Automatic Dosimeter Nebulization," *European J. Resp. Dis.*, vol. 71, (1987), pp. 145–152.

J.S. Patton et al., Pulmonary Delivery of Peptides ad Proteins for Systemic Action,: *Advanced Drug Delivery Reviews*, (1992) vol. 8, pp. 179–196.

M.J. Pikal, "Polymorphism in Pharmaceutical Solids," AAPS, Annual Meeting and Exposition, Nov. 15–19, 1992.

A.N. Pittman et al., "Pneumatic Conveying of Bulk Solids Using a Vacuum Aerated Feed Nozzel," Solids Handling Converence, (1986), Paper C4, pp. C–41 to C–51.

A.R.G. Rao, "Aerosol Insulin Inhalation Enquiry," *Indian J. Physiol, Pharmacol.*, vol. 3, (1959), pp. 161–167.

M.A. Rosenfeld et al., "Adenovirus=Mediated Transfer of a Recombinant al–Antitrypsin Gene to the Lung Epithelium in Vivo," *Science*, vol. 252, Apr. 19, 1991, pp. 431–434.

L. Ryden et al., "Effect of Polymers and Micospheres on the Nasal Absorption of Insulin Rats," *Int'l. J. of Pharmaceuticals*, vol. 83, (1992), pp. 1–10.

F.M. Sakr, "A New Approach for Insulin Delivery via the Pulmonary Route: Design and Pharmacokinetics in Non–Diabetic Rabbits," *Int'l J. of Pharmaceuticals*, vol. 86, (1992), pp. 1–7.

K.J. Schluter et al., Abstract Reproduction Form for Annual Meeting Program Published in Diabetes, vol. 13, No. 6, (1987) pp. 230–232.

R. Stribling et al., "The Mouse as a Model for Cationic Liposome–Based, Aerosolized Gene Delivery," J. Biopharmaceutical Sciences, 3(1/2), pp. 255–263.

S.L. Underwood et al., "A Novel Technique for the Administration of Bronchodilator Drugs Formulated as Dry Powders to the Anaesthetized Guinea Pig," *J. of Pharmacological Methods*, vol. 26, (1991), pp. 203–210.

F.M. Wigley, "Insulin Across Respiratory Mucosae by Aerosol Delivery," *Diabetes*, vol. 20, No. 8, pp. 552–556.

C.L. Witham et al., "Dry Dispersion with Sonic Velocity Nozzles," Workshop on Dissemination Techniques for Smoke and Ovscurants Chemical Systems Laboratory, Aerdeen Proving Ground, MD, Mar. 14–16, 1983.

H. Yoshida, "Absorption of Insulin Delivered to Rabbit Trachea Using Aerosol Dosage Form," *J. of Pharmaceutical Sciences*, vol. 68, No. 5, 1979, pp. 670–671.

V.M. Zholob et al., "Effect of Injector Unit Design on the Particle Size Atomized Powder," Translated from Poroshkovaya Metallurgiya, No. 6 (198), pp. 13–16, Jun. 1979.

\* cited by examiner

DEVICES COMPOSITIONS AND METHODS FOR THE PULMONARY DELIVERY OF AEROSOLIZED MEDICAMENTS

BACKGROUND OF THE INVENTION

This application is a continuation in part of the following U.S. patent applications: Ser. No. 07/910,048, filed Jul. 8, 1992; Ser. No. 08/417,507, filed Apr. 4, 1995, now abandoned, which is a file wrapper continuation of Ser. No. 08/044,358, filed Apr. 7, 1993; Ser. No. 08/232,849, filed Apr. 25, 1994; Ser. No. 08/309,691, filed Sep. 21, 1994; Ser. No. 08/246,034, filed May 18, 1994; Ser. No. 08/313,707, filed Sep. 27, 1994; and Ser. No. 08/383,475, filed Feb. 1, 1995, the full disclosures of which are incorporated herein by reference.

1. Field of the Invention

The present invention relates generally to methods and compositions for the dry powder formulation of pharmaceuticals, including macromolecules, for pulmonary delivery.

Over the years, certain drugs have been sold in compositions suitable for forming a drug dispersion for oral inhalation (pulmonary delivery) to treat various conditions in humans. Such pulmonary drug delivery compositions are designed to be delivered by inhalation by the patient of a drug dispersion so that the active drug within the dispersion can reach the lung. It has been found that certain drugs delivered to the lung are readily absorbed through the alveolar region directly into blood circulation. Pulmonary delivery is particularly promising for the delivery of macromolecules (proteins, polypeptides and nucleic acids) which are difficult to deliver by other routes of administration. Such pulmonary delivery can be effective both for systemic delivery and for localized delivery to treat diseases of the lungs.

Pulmonary drug delivery can itself be achieved by different approaches, including liquid nebulizers, aerosol-based metered dose inhalers (MDI's), and dry powder dispersion devices. Aerosol-based MDI's are losing favor because they rely on the use of chlorofluorocarbons (CFC's), which are being banned because of their adverse effect on the ozone layer. Dry powder dispersion devices, which do not rely on CFC aerosol technology, are promising for delivering drugs that may be readily formulated as dry powders. Many otherwise labile macromolecules may be stably stored as lyophilized or spray-dried powders by themselves or in combination with suitable powder carriers. The ability to deliver pharmaceutical compositions as dry powders, however, is problematic in certain respects. The dosage of many pharmaceutical compositions is often critical so it is necessary that any dry powder delivery system be able to accurately, precisely, and reliably deliver the intended amount of drug. Moreover, many pharmaceutical compositions are quite expensive. Thus, the ability to efficiently deliver the dry powders with a minimal loss of drug is critical. It is also essential that the powder be readily dispersible prior to inhalation by the patient in order to assure adequate distribution and systemic absorption.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are less than 10 $\mu$m in size, usually in the range from 1 $\mu$m to 5 $\mu$m, making powder handling and dispersion more difficult than with larger particles. The problems are exacerbated by the relatively small volumes of pressurized gas, which are available using hand-actuated pumps. In particular, venturi dispersion devices are unsuitable for difficult-to-disperse powders when only small volumes of pressurized gas are available. Another requirement for hand-held and other powder delivery devices is efficiency. It is important that the concentration of drug in the bolus of gas be relatively high to reduce the number of breaths required to achieve a total dosage. The ability to achieve both adequate dispersion and small dispersed volumes is a significant technical challenge that requires in part that each unit dosage of the powdered composition be readily and reliably dispersible.

2. Description of the Relevant Literature

Dry powder dispersion devices for medicaments are described in a number of patent documents. U.S. Pat. No. 3,921,637 describes a manual pump with needles for piercing through a single capsule of powdered medicine. The use of multiple receptacle disks or strips of medication is described in EP467172 (where a reciprocatable punch is used to open a blister pack); WO91/02558; WO93/09832; U.S. Pat. Nos. 4,627,432; 4,811,731; 5,035,237; 5,048,514; 4,446,862; 5,048,514; and 4,446,862. Other patents which show puncturing of single medication capsules include U.S. Pat. Nos. 4,338,931; 3,991,761; 4,249,526; 4,069,819; 4,995,385; 4,889,114; and 4,884,565; and EP469,814; WO90/07351 describes a hand-held pump device with a loose powder reservoir.

A dry powder sonic velocity disperser is described in Witham and Gates, Dry Dispersion with Sonic Velocity Nozzles, presented at the workshop on Dissemination Techniques for Smoke and Obscurants, Chemical Systems Laboratory, Aberdeen Proving Ground, Md., Mar. 14–16, 1983.

U.S. Pat. Nos. 4,926,852 and 4,790,305, describe a type of "spacer" for use with a metered dose inhaler. The spacer defines a large cylindrical volume which receives an axially directed burst of drug from a propellant-driven drug supply. U.S. Pat. No. 5,027,806, is an improvement over the '852 and '305 patents, having a conical holding chamber which receives an axial burst of drug. U.S. Pat. No. 4,624,251, describes a nebulizer connected to a mixing chamber to permit a continuous recycling of gas through the nebulizer. U.S. Pat. No. 4,677,975, is described above. European patent application 347,779 describes an expandable spacer for a metered dose inhaler having a one-way valve on the mouthpiece. WO 90/07351 describes a dry powder oral inhaler having a pressurized gas source (a piston pump) which draws a measured amount of powder into a venturi arrangement.

The respiratory delivery of aerosolized aqueous insulin solutions is described in a number of references, beginning with Gänsslen (1925) *Klin. Wochenschr.* 4:71 and including Laube et al. (1993) *JAMA* 269:2106–21–9; Elliott et al. (1987) *Aust. Paediatr. J.* 23:293–297; Wigley et al. (1971) *Diabetes* 20:552–556. Corthorpe et al. (1992) *Pharm Res* 2:764–768; Govinda (1959) *Indian J. Physiol. Pharmacol.* 3:161–167; Hastings et al. (1992) *J. Appl. Physiol.* 73:1310–1316; Liu et al. (1993) *JAMA* 26:2106–2109; Nagano et al. (1985) *Jikeiklai Med. J.* 32:503–506; Sakr (1992) *Int. J. Phar.* 86:1–7; and Yoshida et al. (1987) *Clin. Res.* 35:160–166. Pulmonary delivery of dry powder medicaments, such as insulin, in a large particle carrier vehicle is described in U.S. Pat. No. 5,254,330. A metered dose inhaler (MDI) for delivering crystalline insulin suspended in a propellant is described in Lee and Sciara (1976) J. Pharm. Sci. 65:567–572. A MDI for delivering insulin into a spacer for regulating inhalation flow rate is described in U.S. Pat. No. 5,320,094. The intrabronchial administration of recombinant insulin is briefly described in Schlüter et al. (Abstract) (1984) Diabetes 33:75A and Köhler et al. (1987) Atemw. Lungenkrkh. 13:230–232. Intranasal and respiratory delivery of a variety of polypeptides, including insulin, in the presence of an enhancer, are described in U.S. Pat. No. 5,011,678 and Nagai et al. (1984) J. Contr. Rel. 1:15–22. Intranasal delivery of insulin in the presence of enhancers and/or contained in controlled release formulations are described in U.S. Pat. Nos. 5,204,108; 4,294,829; and 4,153,689; PCT Applications WO 93/02712, WO 91/02545, WO 90/09780, and WO 88/04556; British Patent 1,527,605; Rydén and Edman (1992) Int. J. Pharm. 83:1–10; and Björk and Edman (1988) Int. J. Pharm. 47:233–238. The preparation and stability of amorphous insulin were described by Rigsbee and Pikal at the American Association of Pharmaceutical Sciences (AAPS), Nov. 14–18, 1993, Lake Buena Vista, Fla. Methods for spray drying polypeptide, polynucleotide and other labile drugs in a carrier which forms an amorphous structure which stabilizes the drug are described in European patent application 520 748. (AAPS), Nov. 14–18, 1993, Lake Buena Vista, Fla.

Stribling et al. (1992) J. Biopharm. Sci. 3:255–263, describes the aerosol delivery of plasmids carrying a chloramphenicol acetyltransferase (CAT) reporter gene to mice. The plasmids were incorporated in DOTMA or cholesterol liposomes, and aqueous suspensions of the liposomes were nebulized into a small animal aerosol delivery chamber. Mice breathing the aerosol were found to at least transiently express CAT activity in their lung cells. Rosenfeld et al. (1991) Science: 252:431–434, describes the in vivo delivery of an alpha-1 antitrypsin gene to rats, with secretion of the gene product being observable for at least one week. The gene was diluted in saline and instilled directly into the rat trachea. Friedman (1989) Science 244:1275–1281 is a review article describing human gene therapy strategies.

U.S. Pat. Nos. 4,833,125 and 4,698,328, describe the administration of active parathyroid hormone fragments in combination with vitamin D or a dietary calcium supplement. Suggested administration routes include parenteral by injection, rapid infusion, nasopharyngeal absorption, dermal absorption, or oral. See also, Neer et al. (1987) Osteoporosis 53:829–835. U.S. Pat. No. 5,011,678, describes the use of amphophilic steroids as a penetration enhancer for nasal or bronchopulmonary delivery of proteins and polypeptides, listing parathyroid hormone as one of a "veritable host" of proteins which could be delivered with the enhancer. Parathyroid hormone (full length) is secreted naturally from the parathyroid gland as a series of spikes in a pulsatile fashion which is analogous to pituitary hormones (Harms et al. (1987) Int. Symp. on Osteoporosis, Aalborg, Abstract 232). The full length hormone is rapidly broken down in the circulation into several fragments which are the dominant serum forms. It is hypothesized that an intermittent or pulsatile secretion pattern for parathyroid hormone is necessary to maintain its bone restoring properties (Hesch et al. (1988) Calcif. Tissue Int. 42:341–344 and Habener et al. (1971). Proc. Natl. Acad. Sci USA 68:2986–2991). Patton and Platz (1992) Adv. Drug Deliver. Rev. 8:179–196, describe methods for delivering proteins and polypeptides by inhalation through the deep lung.

The aerosolization of protein therapeutic agents, including alpha-1 antitrypsin, is disclosed in EP0289336. The use of alpha-1 antityrpsin for treating pulmonary inflammation is disclosed in U.S. Pat. No. 5,093,316.

Therapeutic aerosol formulations, including calcitonin, are disclosed in WO90/09781.

Methods and compositions for inhibiting neutrophil elastase and cathespin G employing aerosolized 2-0-desulfated heparin is disclosed in WO94/02107.

Interleukin-1 receptor compositions are disclosed in U.S. Pat. Nos. 4,968,607, 5,081,228 and 5,180,812.

Aerosol formulations of interferons have been produced for pulmonary delivery as described in WO 91/16038. WO 91116038 teaches adding a surfactant or the like to improve the dispersibility of a human interferon from a CFC delivery system. Methods and compositions for the preparation of solid polypeptide microparticles as a pharmaceutical aerosol formulation are disclosed in WO 91/16038. The purification of proteins of molecular weight in excess of 12,000, including human IFN is disclosed in U.S. Pat. No. : 4,503,035. Low pH pharmaceutical compositions of recombinant IFN-beta are disclosed in WO 89/05158.

3. Objects of the Invention

An object of the present invention is to provide a pharmaceutical composition suitable for long-term pulmonary administration to a patient in need thereof.

Another object of this invention is to provide a pharmaceutical-containing dispersible dry powdered composition that is administered by inhalation in a manner that is free of a liquid propellant such as a CFC, HFC or carbon dioxide.

Another object of this invention is to provide a pharmaceutical-containing dispersible dry powdered composition that can be easily manufactured by a method that maintains a high percentage of pharmaceutical activity.

Another object of this invention is to provide a manufacturable method for the production of pharmaceutical composition of sufficient purity.

Still another object of this invention is to provide a pharmaceutical-containing dispersible dry powdered composition that exhibits a high level of stability.

Other objects may be apparent to one of ordinary skill upon reviewing the following specification and claims.

SUMMARY OF THE INVENTION

According to the subject invention, dispersible dry powder pharmaceutical-based compositions are provided, including methods for their manufacture and dry powder dispersion devices. A dispersible dry powder pharmaceutical-based composition is one having a moisture content of less than about 10% by weight (% w) water, usually below about 5% w and preferably less than about 3% w; a particle size of about 1.0–5.0 $\mu$m mass median diameter (MMD), usually 1.0–4.0 $\mu$m MMD, and preferably 1.0–3.0 $\mu$m MMD; a delivered dose of about >30%, usually >40%, preferably >50%, and most preferred >60%; and an aerosol particle size distribution of about 1.0–5.0 $\mu$m mass median aerodynamic diameter (MMAD), usually 1.5–4.5 $\mu$m MMAD, and preferably 1.5–4.0 MMAD. Such composition are of pharmaceutical grade purity.

DESCRIPTION OF SPECIFIC EMBODIMENTS

The present invention is based at least in part on the dispersibility characteristics of the pharmaceutical-based dry powder compositions produced according to the present invention. The dispersibility characteristics of the subject pharmaceutical-based compositions means that they are more suitable for use in pulmonary delivery devices than compositions prepared by other methods. The compositions of the invention are readily aerosolized and rapidly absorbed through the lungs of a host when delivered by a dry powder inhaler.

DEFINITIONS

In interpreting the claims to the various aspects of this invention, there are several important definitons that should be considered.

The term "dispersibility" or "dispersible" means a dry powder having a moisture content of less than about 10% by weight (% w) water, usually below about 5% w and preferably less than about 3% w; a particle size of about 1.0–5.0 $\mu$m mass median diameter (MMD), usually 1.0–4.0 $\mu$m MMD, and preferably 1.0–3.0 $\mu$m MMD; a delivered dose of about >30%, usually >40%, preferably >50%, and most preferred >60%; and an aerosol particle size distribution of about 1.0–5.0 $\mu$m mass median aerodynamic diameter (MMAD), usually 1.5–4.5 $\mu$m MMAD, and preferably 1.5–4.0 MMAD. Methods and compositions for improving dispersibility are disclosed in U.S. application Ser. No.: 08/423,568, filed Apr. 14, 1995, now abandoned, the disclosures of which are hereby incorporated by reference.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns ($\mu$m) in diameter with a relatively uniform spheroidal shape distribution. More preferably the diameter is less than about 7.5 $\mu$m and most preferably less than about 5.0 $\mu$m. Usually the particle size distribution is between about 0.1 $\mu$m and about 5 $\mu$m in diameter, particularly about 0.3 $\mu$m to about 5 $\mu$m.

The term "dry" means that the composition has a moisture content such that the particles are readily dispersible in an inhalation device to form an aerosol. This moisture content is generally below about 10% by weight (% w) water, usually below about 5% w and preferably less than about 3% w.

The term "therapeutically effective amount" is the amount present in the composition that is needed to provide the desired level of drug in the subject to be treated to give the anticipated physiological response. This amount is determined for each drug on a case-by-case basis. Guidelines are given hereafter.

The term "physiologically effective amount" is that amount delivered to a subject to give the desired palliative or curative effect. This amount is specific for each drug and its ultimate approved dosage level. Guidelines are given hereafter.

The term "pharmaceutically acceptable carrier" means that the carrier can be taken into the lungs with no significant adverse toxicological effects on the lungs.

COMPOSITIONS OF THE INVENTION

One aspect of this invention is a dispersible pharmaceutical-based dry powder composition for pulmonary delivery, the composition comprising a therapeutically effective amount of a pharmaceutical in combination with a pharmaceutically acceptable carrier.

In general, the compositions of this invention have a suitable for pulmonary delivery because of their dispersibility characteristics. Such compositions were not previously known in the art. In the dry state, the pharmaceutical may be in crystalline or amorphous form. Some examples of pharmaceutical compositions suitable for formulation into dispersible dry powders are listed in Table 1. These include macromolecule and non-macromolecule-based pharmaceuticals, usually macromolecules, with insulin, interleukin-1 receptor, parathyroid hormone (PTH-34), alpha-1 antitrypsin, calcitonin, low molecular weight heparin, heparin, interferon, and nucleic acids being preferred.

A therapeutically effective amount of active pharmaceutical will vary in the composition depending on the biological activity of the drug employed and the amount needed in a unit dosage form. Because the subject compounds are dispersible, it is highly preferred that they be manufactured in a unit dosage form in a manner that allows for ready manipulation by the formulator and by the consumer. This generally means that a unit dosage will be between about 0.5 mg and 15 mg of total material in the dry powder composition, preferably between about 2 mg and 10 mg. Generally, the amount of drug in the composition will vary from about 0.05% w to about 99.0% w. Most preferably the composition will be about 0.2% to about 97.0% w drug.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. Preferably about 5% w to about 95% w will be used.

The carrier may be one or a combination of two or more pharmaceutical excipients, but will generally be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the present invention are readily absorbed in the lungs without the need to employ penetration enhancers.

The types of pharmaceutical excipients that are useful as carriers in this invention include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

It has been found that HSA is particularly valuable as a carrier in that it provides improved dispersibility.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, lucine, phenylalanine, and the like.

Suitable pH adjusters or buffers include organic salts prepared from organic acids and bases, such as sodium citrate, sodium ascorbate, and the like; sodium citrate is preferred.

The unit dosage form, method of treatment, and process of preparation of this invention are described hereafter.

Unit Dosage Form.

Another aspect of this invention is a unit dosage form for pulmonary delivery of dispersible dry powder pharmaceutical-based compositions, which dosage form comprises a unit dosage receptacle containing a pharmaceutical-based dry powder composition, which composition comprises a therapeutically effective amount of a pharmaceutical in combination with a pharmaceutically acceptable carrier.

In this aspect of the invention, the composition of this invention (as discussed hereinbefore) is placed within a suitable dosage receptacle in an amount sufficient to provide a subject with drug for a unit dosage treatment. The dosage receptacle is one that fits within a suitable inhalation device to allow for the aerosolization of the interferon-based dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with Glaxo's Ventolin Rotohaler brand powder inhaler or Fison's Spinhaler brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

Method of Treating a Disease State.

Another aspect of this invention is a method of treating a condition responsive to treatment by a pharmaceutical of interest, which method comprises pulmonarily administering to a subject in need thereof a physiologically effective amount of a dispersible pharmaceutical-based dry powder composition that comprises a therapeutically effective amount of drug in combination with a pharmaceutically acceptable carrier.

Conditions that may be treated by the compositions of this are described in Table 1.

The physiologically effective amount needed to treat a particular condition or disease state will depend on the individual, the condition, length of treatment, the regularity of treatment, the type of drug, and other factors, but can be determined by one of ordinary skill in the medicinal arts.

It is presently believed that the effective absorption by a host of dry powder composition according to the present invention results from a rapid dissolution in the ultra-thin (<0.1 μm) fluid layer of the alveolar lining of the lung. The particles of the present invention thus have a mean size which is from 10 to 50 times larger than the lung fluid layer, making it unexpected that the particles are dissolved and the interferon systemically absorbed in a rapid manner for either local lung or systemic treatment An understanding of the precise mechanism, however, is not necessary for practicing the present invention as described herein.

The aerosolized pharmaceutical-based dry powders of this invention are particularly useful in place of parenteral delivery. Thus, the methods and compositions of the present invention will be particularly valuable in chronic treatment protocols where a patient can self-medicate. The patient can achieve a desired dosage by inhaling an appropriate amount of drug, as just described. The efficiency of systemic delivery via the method as just described will typically be in the range from about 15% to 50%.

Method for Aerosolizing the Powder.

Still another aspect of this invention is a device and method for aerosolizing a pharmaceutical-based dry powder composition that comprises a therapeutically effective amount of drug in combination with a pharmaceutically acceptable carrier, which method comprises dispersing an amount of the dry powder composition in a gas stream to form an aerosol and capturing the aerosol in a chamber having a mouthpiece for subsequent inhalation by a patient.

A further detailed description of this method is found in pending U.S. patent application Ser. Nos.: 07/910,048 and 08/207,472, both of which are incorporated herein by reference.

Preparing the Compositions.

Still another aspect of this invention is a method for preparing a dispersible pharmaceutical-based dry powder composition of this invention that comprises spray drying an aqueous mixture of the drug and a pharmaceutically acceptable carrier under conditions to provide a respirable dry powder composition.

Spray drying is a process in which a homogeneous aqueous mixture of drug and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. Preferably the aqueous mixture is a solution. The solvent, generally water, rapidly evaporates from the droplets producing a fine dry powder having particles 1 to 5 μm in diameter. Surprisingly, the drug is not degraded when it is exposed to the hot drying gas, and the interferon powders can be prepared having sufficient purity for pharmaceutical use. An acceptable purity is defined as less than 5% degradation products and contaminates, preferably less than 3% and most preferably less than 1%.

The spray drying is done under conditions that result in substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 μm or less with about 90% of the mass being in particles having a diameter less than 5 μm. Alternatively, about 95% of the mass will have particles with a diameter of less than 10 μm with about 80% of the mass of the particles having a diameter of less than 5 μm.

The solutions may then be sprayed dried in conventional spray drying equipment from commercial suppliers, such as Buchi, Niro, Yamato Chemical Co., Okawara Kakoki Co., and the like, resulting in a substantially amorphous particulate product.

For the spraying process, such spraying methods as rotary atomization, pressure atomization and two-fluid atomization can be used. Examples of the devices used in these processes include "Parubisu [phonetic rendering] Mini-Spray GA-32" and "Parubisu Spray Drier DL41", manufactured by Yamato Chemical Co., or "Spray Drier CL-8," "Spray Drier L-8," "Spray Drier FL-12," "Spray Drier FL-16" or "Spray Drier FL-20," manufactured by Okawara Kakoki Co., can be used for the method of spraying using rotary-disk atomizer.

While no special restrictions are placed on the nozzle of the atomizer used in the process of spraying, it is recommended to use a nozzle which can produce a spray-dry composition with a grain diameter suitable for nasal, pharyngeal or pulmonary administration. For example, nozzle types "1A," "1," "2A," "2," "3" and the like, manufactured by Yamato Chemical Co., can be used for the above-mentioned spray-drier, manufactured by the same company. In addition, disks type "MC-50," "MC-65" or "MC-85," manufactured by Okawara Kakoki Co., can be used as rotary disks of the spray-drier atomizer, manufactured by the same company.

While no particular restrictions are placed on the gas used to dry the sprayed material, it is recommended to use air, nitrogen gas or an inert gas. The temperature of the inlet of the gas used to dry the sprayed materials such that it does not cause heat deactivation of the sprayed material. The range of temperatures may vary between about 50° C. to about 200° C., preferably between about 50° C. and 100° C. The temperature of the outlet gas used to dry the sprayed material, may vary between about 0° C. and about 150°, preferably between 0° C. and 90° C., and even more preferably between 0° C. and 60° C. The fact that inlet and outlet temperatures above about 55° C. can be used is surprising in view of the fact that most macromolecule-based drugs deactivate at that temperature, with nearly complete deactivation occurring at about 70° C.

The dispersible pharmaceutical-based dry powders of the present invention may optionally be combined with pharmaceutical carriers or excipients which are suitable for respiratory and pulmonary administration. Such carriers may serve simply as bulking agents when it is desired to reduce the interferon concentration in the powder which is being delivered to a patient, but may also serve to enhance the stability of the interferon compositions and to improve the dispersibility of the powder within a powder dispersion device in order to provide more efficient and reproducible delivery of the interferon and to improve handling characteristics of the interferon such as flowability and consistency to facilitate manufacturing and powder filling.

Such carrier materials may be combined with the drug prior to spray drying, i.e., by adding the carrier material to the purified bulk solution. In that way, the carrier particles will be formed simultaneously with the drug particles to produce a homogeneous powder. Alternatively, the carriers may be separately prepared in a dry powder form and combined with the dry powder drug by blending. The powder carriers will usually be crystalline (to avoid water absorption), but might in some cases be amorphous or mixtures of crystalline and amorphous. The size of the carrier particles may be selected to improve the flowability of the drug powder, typically being in the range from 25 μm to 100 μm. A preferred carrier material is crystalline lactose having a size in the above-stated range.

Alternatively, dry powder compositions may be prepared by other processes such as lyophilization and jet milling as disclosed in WO 91/16038, the disclosures of which are hereby incorporated by reference.

TABLE 1

| DRUG | INDICATIONS |
|---|---|
| SELECTED MACROMOLECULE DRUGS FOR SYSTEMIC APPLICATIONS | |
| Calcitonin | Osteoporosis Prophylaxis |
| | Paget's Disease |
| | Hypercalcemia |
| Erythropoietin (EPO) | Anemia |
| Factor IX | Hemophilia B |
| Granulocyte Colony Stimulating Factor (G-CSF) | Neutropenia |
| Granulocyte Macrophage Colony Stimulating Factor (GM-CSF) | Bone Marrow Engraftment/ Transplant Failure |
| Growth Hormone | Short Stature |
| | Renal Failure |
| Heparin | Blood Clotting |
| Heparin (Low Molecular Weight) | Blood Clotting |
| Insulin | Type I and Type II Diabetes |
| Interferon Alpha | Hepatitis B and C |
| | Hairy Cell Leukemia |
| | Kaposi's Sarcoma |
| Interferon Beta | Multiple Sclerosis |
| Interferon Gamma | Chronic Granulomatous Disease |
| Interleukin-2 | Renal Cancer |
| Luteinizing Hormone Releasing Hormone (LHRH) | Prostate Cancer Endometriosis |
| Somatostatin Analog | Gastrointestinal Cancers |
| Vasopressin Analog | Diabetes Insipidus |
| | Bed Wetting |
| FSH | Fertility |
| Amylin | Type I Diabetes |
| Ciliary Neurotrophic Factor | Lou Gehrig's Disease |
| Growth Hormone Releasing Factor (GRF) | Short Stature |
| Insulin-Like Growth Factor | Osteoporosis |
| | Nutritional Support |
| Insulinotropin | Type II Diabetes |
| Interferon Beta | Hepatitis B and C |
| Interferon Gamma | Rheumatoid Arthritis |
| Interleukin-1 Receptor Antagonist | Rheumatoid Arthritis |
| Interleukin-3 | Adjuvant to Chemotherapy |
| Interleukin-4 | Immunodeficiency Disease |
| Interleukin-6 | Thrombocytopenia |
| Macrophage Colony Stimulating Factor (M-CSF) | Fungal Disease |
| | Cancer |
| | Hypercholesterolemia |
| Nerve Growth Factor | Peripheral Neuropathies |
| Parathyroid Hormone | Osteoporosis |
| Somatostatin Analog | Refractory Diarrheas |
| Thymosin Alpha 1 | Hepatitis B and C |
| IIb/IIIa Inhibitor | Unstable Angina |
| Alpha-1 Antitrypsin | Cystic Fibrosis |
| Anti-RSV Antibody | Respiratory Syncytial Virus |
| Cystic Fibrosis Transmembrane Regulator (CFTR) Gene | Cystic Fibrosis |
| Deoxyribonuclease (DNase) | Chronic Bronchitis |
| Heparin | Asthma |
| Bactericidal/Permeability Increasing Protein (BPI) | Adult Respiratory Distress Syndrome (ARDS) |
| Anti-CMV Antibody | Cytomegalovirus |

TABLE 1-continued

| DRUG | INDICATIONS |
| --- | --- |
| Interleukin-1 Receptor | Asthma |
| SELECTED NON-MACROMOLECULE DRUGS FOR SYSTEMIC AND LOCAL LUNG APPLICATIONS | |
| Pentamidine isethiouate | Pneumocystis carini peneumonia |
| Albuterol sulfate | Broncospasm |
| Metaproterenol sulfate | Bronchial asthma |
| Beclomethasone diprepionate | |
| Trimcinoline acetomide | |
| Budesonide acetonide | |
| Ipratropium bromide | |
| Flunisolide | |
| Cromolyn sodium | |
| Ergotamine Tartrate | Migranes |

The following examples are offered by way of illustration and not limitation.

EXPERIMENTAL

According the the subject invention, the following dispersible dry powder formulations were prepared as described. All compositions produced according to the present invention meet the strict specifications for content and purity required of pharmaceutical products.

EXAMPLE I 20.0% Insulin Formulation for Pulmonary Delivery

A. Formulation

Bulk crystalline human zinc insulin, was obtained from Eli Lilly and Company, Indianapolis, IN. A 20% insulin formulation was acheived by combining 1.5 mg insulin per 1.0 mL deionized water with 4.96 mg/mL USP mannitol and 1.04 mg/mL citrate buffer(sodium citrate dihydrate USP and citric acid monohydrate USP) for a total solids concentration of 7.5 mg/mL at pH 6.7±0.3.

B. Spray Drying

A dry powder of the 20% insulin formulation described above was produced by spray drying the aqueous mixture using a Buchi Laboratory Spray Dryer under the following conditions:

| Temperature of aqueous mixture | 2–8° C. |
| --- | --- |
| Inlet temperature | 120–122° C. |
| Feed rate | 5.3 mL/min |
| Outlet temperature | 80–81° C. |

Once the aqueous mixture was consumed, the outlet temperature was maintained at <80° C. for about 10 minutes by slowly decreasing the inlet temperature to provide a secondary drying.

C. Characterization

The above 20% insulin dry powder composition contained 66.1% mannitol and 13.9% citrate. The composition was found to contain 1.1 to 2.0% moisture as measured by a coulombic Karl Fischer method using a Mitsubishi CA-06 Moisture Meter.

The particle size distribution of the composition was measured by liquid centrifugal sedimentation in a Horiba CAPA-700 Particle Size Analyzer following dispersion of the powder on Sedisperse A-11 (Micrometrics, Norcross, Ga.) and was determined to be 1.3 $\mu$m to 1.5 $\mu$m MMD.

The delivered dose of the insulin powder composition was measured by collecting the aerosol powder produced by a dry powder dispersion device, similar to devices described in co-pending U.S. application Ser. Nos. 07/910,048; 08/313,707; 08/309,691 and PCT/US92/05621, the disclosures of which are hereby incorporated by reference, on a filter placed over the device mouthpiece. The delivered dose of the insulin powder composition was determined to be 563±16 $\mu$g or 60 to 64% of the total powder (5.0 mg) loaded into the device.

The aerosol particle size distribution, measured using a cascade impactor (California Measurements IMPAQ-6), was determined to be 2.0 $\mu$m MMAD, with 86% to 90% of the particles <5.0 $\mu$m in diameter.

The insulin content of the powder, measured by reverse phase HPLC (rpHPLC) was determined to be 197 $\mu$g/mg powder, accounting for 99% of the expected insulin. No degradation peaks were detected in the chromatogram.

EXAMPLE II 5.0% Parathyroid Hormone Formulation for Pulmonary Delivery

A. Formulation

Bulk 34 amino acid active fragment of parathyroid hormon, PTH (1–34), was obtained from BACHEM CALIFORNIA, Torrance, Calif. A 5.0% PTH (1–34) formulation was acheived by combining 0.375 mg PTH (1–34) per 1.0 mL deionized water with 6.06 mg/mL mannitol USP and 1.04 mg/mL citrate buffer (sodium citrate dihydrate USP and citric acid monohydrate USP) for a total solids concentration of 7.48 mg/mL at pH 6.3.

B. Spray Drying

A dry powder of the 5.0% PTH (1–34) formulation described above was produced by spray drying the aqueous mixture using a Buchi Laboratory Spray Dryer under the following conditions:

| Temperature of aqueous mixture | 2–8° C. |
| --- | --- |
| Inlet temperature | 122–124° C. |
| Feed rate | 5.2 mL/min |
| Outlet temperature | 73–74° C. |

Once the aqueous mixture was consumed, the outlet temperature was maintained at <80° C. for about 5 minutes by slowly decreasing the inlet temperature to provide a secondary drying.

C. Characterization

The following characterization of the dry powder formulation described above was carried out using the methods described in Example I unless indicated otherwise.

The above 5.0% PTH (1–34) dry powder composition contained 81.0% mannitol and 13.9% citrate. The formulation contained 0.5% moisture.

The particle size distribution of the composition was determined to be 2.4 $\mu$m and 2.7 $\mu$m MMD in separate measurements.

The delivered dose of the PTH (1–34) powder was determined to be 161 $\mu$g or 64.5% and 175 $\mu$g or 69.2% in separate measurements.

The PTH (1–34) content of the powder, measured by rpHPLC was determined to be 48.5 $\mu$g/mg powder, accounting for 97% of the expected value. No degradation peaks were detected in the chromatogram.

EXAMPLE III

0.7% Interleukin-1 Receptor Formulation for Pulmonary Delivery

A. Formulation

Bulk interleukin-1 receptor, IL-1 receptor, was obtained from Immunex Corporation, Seattle, Wash. A 0.7% IL-1 receptor formulation was acheived by combining 0.053 mg IL-1 receptor per 1.0 mL deionized water with 7.07 mg/mL raffinose (Pfanstiehl, Waukegan, Ill.) and 0.373 mg/mL Tris buffer at pH 7.18.

B. Spray Drying

A dry powder of the 0.7% IL-1 receptor formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 135–137° C. |
| Feed rate | 4.9 mL/min |
| Outlet temperature | 92–93° C. |

Once the aqueous mixture was consumed, the outlet temperature was maintained at 90° C. for about 15 minutes by slowly decreasing the inlet temperature to provide a secondary drying.

C. Characterization

The following characterization of the dry powder formulation described above was carried out using the methods described in Example I unless indicated otherwise.

The above 0.7% IL-1 receptor dry powder composition contained 94.3% raffinose and 5.0% Tris. The formulation contained 1.84±0.25% moisture.

The particle size distribution of the composition was determined to be 1.95 $\mu$m MMD with 100% of the particles <5.0 $\mu$m.

The delivered dose of the IL-1 receptor powder was determined to be 22.3±2.0 $\mu$g or 53.4±4.7%.

The aerosol particle size distribution, was determined to be 3.2 $\mu$m MMAD, with 77% of the particles <5.0 $\mu$m in diameter.

The IL-1 receptor content of the powder as measured by rpHPLC was determined to be 8.4 $\mu$g/mg, accounting for 120% of the expected IL-1 receptor. No degradation peaks were detected in the chromatogram.

EXAMPLE IV

5.0% Interleukin-1 Receptor Formulation for Pulmonary Delivery

A. Formulation

Bulk interleukin-1 receptor, IL-1 receptor, was obtained from Immunex Corporation, Seattle, Wash. A 5.0% IL-1 receptor formulation was acheived by combining 0.375 mg IL-1 receptor per 1.0 mL deionized water with 6.77 mg/mL raffinose and 0.351 mg/mL Tris buffer at pH 7.35.

B. Spray Drying

A dry powder of the 5.0% IL-1 receptor formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 138° C. |
| Feed rate | 4.9 mL/min |
| Outlet temperature | 91° C. |

Once the aqueous mixture was consumed, the outlet temperature was maintained at 90° C. for about 15 minutes by slowly decreasing the inlet temperature to provide a secondary drying.

C. Characterization

The following characterization of the dry powder formulation described above was carried out using the methods described in Example I unless indicated otherwise.

The above 5.0% IL-1 receptor dry powder composition contained 90.3% raffinose and 4.7% Tris. The formulation contained 1.75±0.26% moisture.

The particle size distribution of the composition was determined to be 2.74 $\mu$m MMD with 97% of the particles <5.0 $\mu$m.

The delivered dose of the IL-1 receptor powder was determined to be 123.4±24.5 $\mu$g or 49.3±9.8%.

The aerosol particle size distribution, was determined to be 4.1 $\mu$m MMAD, with 64% of the particles <5.0 $\mu$m in diameter.

The IL-1 receptor content of the powder as measured by rpHPLC was determined to be 52.7±1.8 $\mu$g/mg, accounting for 105% of the expected IL-1 receptor. No degradation peaks were detected in the chromatogram.

EXAMPLE V

26.7% Human Calcitonin Formulation for Pulmonary Delivery

A. Formulation

Bulk human calcitonin was obtained from Ciba-Geigy. A 26.7% human calcitonin formulation was acheived by combining 1.9 mg human calcitonin per 1.0 mL deionized water with 4.3 mg/mL mannitol and 0.9 mg/mL citrate buffer at pH 3.85.

B. Spray Drying

A dry powder of the 26.7% human calcitonin formulation described above was produced by spray drying the aqueous mixture using a Buchi Laboratory Spray Dryer under the following conditions:

| | |
|---|---|
| Temperature of aqueous mixture | 4° C. |
| Inlet temperature | 119° C. |
| Feed rate | 5.5 mL/min |
| Outlet temperature | 78° C. |
| Atomizer coolant temperature | 0–5° C. |
| Cyclone coolant temperature | 25–30° C. |

Once the aqueous mixture was consumed, the outlet temperature was maintained at 80° C. for about 10 minutes by slowly decreasing the inlet temperature to provide a secondary drying.

C. Characterization

The following characterization of the dry powder formulation described above was carried out using the methods described in Example I unless indicated otherwise.

The above 26.7% human calcitonin dry powder composition contained 60% mannitol and 13.3% citrate. The formulation contained 0.71% moisture.

The particle size distribution of the composition was determined to be 1.33±0.63 $\mu$m MMD.

The delivered dose of the human calcitonin powder was determined to be 76.8±6.7%.

The human calcitonin content of the powder as measured by rpHPLC was determined to be 272.0 μg/mg, accounting for 102±1.7% of the expected human calcitonin. No degradation peaks were detected in the chromatogram.

EXAMPLE VI

90% Alpha-1 Antitrypsin Formulation for Pulmonary Delivery

A. Formulation

Bulk alpha-1 antitrypsin, A1A, was obtained from Armour Pharmaceutical Company, Kankakee, Ill. A 90% A1A formulation was acheived by combining 4.89 mg A1A per 1.0 mL deionized water with 0.54 mg/mL citrate buffer at pH 6.0.

B. Spray Drying

A dry powder of the 90% A1A formulation described above was produced by spray drying the aqueous mixture using a Buchi Laboratory Spray Dryer under the following conditions:

| | |
|---|---|
| Temperature of aqueous mixture | 4° C. |
| Inlet temperature | 98–101° C. |
| Feed rate | 5.0 mL/min |
| Outlet temperature | 65° C. |
| Atomizer coolant temperature | 2–8° C. |
| Cyclone coolant temperature | 30° C. |

Once the aqueous mixture was consumed, the outlet temperature was maintained at 69° C. for about 10 minutes by slowly decreasing the inlet temperature to provide a secondary drying.

C. Characterization

The following characterization of the dry powder formulation described above was carried out using the methods described in Example I unless indicated otherwise.

The above 90% A1A dry powder composition contained 10.0% citrate. The formulation contained 4.79% moisture.

The particle size distribution of the composition was determined to be 1.71±0.87 μm MMD.

The delivered dose of the 90% A1A powder was determined to be 67.0±5.0%.

The aerosol particle size distribution, was determined to be 1.0 μm MMAD, with 90% of the particles <5.0 μm in diameter.

The A1A content of the powder as measured by rpHPLC was determined to be 80% of the expected value. No degradation peaks were detected in the chromatogram. The activity after spray drying was determined to be 74±1%

EXAMPLE VII

0.3% Beta Interferon Formulation for Pulmonary Delivery Containing Human Serum Albumin A. Formulation Bulk beta interferon, IFN-β, was obtained from Toray Industries, Inc., Tokyo, Japan. A 0.3% IFN-β formulation was acheived by combining 0.025 mg IFN-β per 1.0 mL deionized water with 5.54 mg/mL human serum albuman (HSA), 2.3 mg/mL citrate buffer and 0.345 mg/mL of NaCl at pH 4.5.

B. Spray Drying

A dry powder of the 0.3% IFN-β formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 93° C. |
| Feed rate | 2.7 mL/min |
| Outlet temperature | 62° C. |

C. Characterization

The following characterization of the dry powder formulation described above was carried out using the methods described in Example I unless indicated otherwise.

The above 0.3% IFN-β dry powder composition contained 66.0% HSA, 27.4% citrate, 4.1% NaCl. The formulation contained 4.22% moisture.

The particle size distribution of the composition was determined to be 1.62 μm MMD with 94.8% of the particles <5 μm.

The delivered dose of the 0.3% IFN-β powder was determined to be 9;9 μg/mg or 66.0±4.0%.

The aerosol particle size distribution, was determined to be 2.0 μm MMAD, with 85% of the particles <5.0 μm in diameter.

The IFN-β activity of the powder as measured by IFN-β enzyme immunoassay (Toray-Fuji Bionics) and was determined to be 109±8% of the expected activity.

EXAMPLE VIII

0.3% Beta Interferon Formulation for Pulmonary Delivery Containing Raffinose A. Formulation Bulk beta interferon, IFN-β, was obtained from Toray Industries, Inc., Tokyo, Japan. A 0.3% IFN-β formulation was acheived by combining 0.025 mg IFN-β per 1.0 mL deionized water with 4.7 mg/mL raffinose, 1.0 mg/mL human serum albuman (HSA), 2.3 mg/mL citrate buffer and 0.3 mg/mL of NaCl at pH 4.5.

B. Spray Drying

A dry powder of the 0.3% IFN-β formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 145° C. |
| Feed rate | 5.0 mL/min |
| Outlet temperature | 87° C. |

Once the aqueous mixture was consumed, the outlet temperature was maintained at 97° C. for about 5 minutes by slowly decreasing the inlet temperature to provide a secondary drying.

C. Characterization

The following characterization of the dry powder formulation described above was carried out using the methods described in Example I unless indicated otherwise.

The above 0.3% IFN-β dry powder composition contained 56.4% raffinose, 11.9% HSA, 27.4% citrate, 3.5% NaCl. The formulation contained 0.69% moisture.

The particle size distribution of the composition was determined to be 2.06 μm MMD with 88.9% of the particles <5 μm.

The delivered dose of the 0.3% IFN-β powder was determined to be 10.2 µg/mg or 68.0±2.0%.

The aerosol particle size distribution, was determined to be 2.5 µm MMAD, with 84% of the particles <5.0 µm in diameter.

The IFN-β activity of the powder as measured by IFN-β enzyme immunoassay (Toray-Fuji Bionics) and was determined to be 109±8% of the expected activity.

EXAMPLE IX

93% Low Molecular Weight Heparin Formulation For Pulmonary Delivery

A. Formulation

Bulk low molecular weight heparin sodium salt (Av. Mol. Wt.: Approx. 6000) from porcine intestinal mucosa, heparin (LMW), was obtained from Sigma Chemical, St. Louis, Mo. A 93% heparin (LMW) formulation was acheived by combining 6.9 mg heparin (LMW) per 1.0 mL deionized water with 0.5 mg/mL HSA at pH 6.9.

B. Spray Drying

A dry powder of the 93% heparin (LMW) formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 140° C. |
| Feed rate | 3.8 mL/min |
| Outlet temperature | 85° C. |
| Atomizer coolant temperature | 2–8° C. |
| Cyclone coolant temperature | 20° C. |

Once the aqueous mixture was consumed, the outlet temperature was maintained at 80° C. for about 10 minutes by slowly decreasing the inlet temperature to provide a secondary drying.

C. Characterization

The following characterization of the dry powder formulation described above was carried out using the methods described in Example I unless indicated otherwise.

The above 93% heparin (LMW) dry powder composition contained 7.0% HSA.

The delivered dose of the 93% heparin (LMW) powder was determined to be 60.0±1.0%.

The aerosol particle size distribution, was determined to be 3.5 µm MMAD, with 70% of the particles <5.0 µm in diameter.

EXAMPLE X

97% Unfractionated Heparin Formulation for Pulmonary Delivery

A. Formulation

Bulk unfractionated heparin sodium salt from porcine intestinal mucosa, heparin, as obtained from Sigma Chemical, St. Louis, Mo. A 97% heparin formulation was acheived by combining 7.0 mg heparin per 1.0 mL deionized water with 0.25 mg/mL HSA at pH 6.55.

B. Spray Drying

A dry powder of the 97% heparin formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 150° C. |
| Feed rate | 4.0 mL/min |
| Outlet temperature | 85° C. |
| Atomizer coolant temperature | 2–8° C. |
| Cyclone coolant temperature | 20° C. |

Once the aqueous mixture was consumed, the outlet temperature was maintained at 80° C. for about 10 minutes by slowly decreasing the inlet temperature to provide a secondary drying.

C. Characterization

The following characterization of the dry powder formulation described above was carried out using the methods described in Example I unless indicated otherwise.

The above 97% heparin dry powder composition contained 3.0% HSA. The formulation contained 5.11% moisture.

The particle size distribution of the composition was determined to be 2.0 to 2.5 µm MMD.

The delivered dose of the 97% heparin powder was determined to be 79.0±6.0%.

The aerosol particle size distribution, was determined to be 3.2 µm MMAD, with 70% of the particles <5.0 µm in diameter.

EXAMPLE XI

Lipid Vector Gene Formulation for Pulmonary Delivery

A. Formulation

Bulk pCMVβ DNA:Lipid vector as described in U.S. application Ser. No. 08/422,563, filed Apr. 14, 1995, now U.S. Pat. No. 5,994,314 entitled COMPOSITIONS AND METHODS FOR NUCLEIC ACID DELIVERY TO THE LUNG, the disclosures of which are hereby incorporated by reference, was obtained from Genzyme Corporation, Cambridge, Mass. A 0.71% DNA:Lipid vector formulation was achieved by combining 0.005:0.03 mg DNA:Lipid vector per 1.0 mL deionized water with 5.3 mg/mL glycine (J. T. Baker) 0.3 mg/mL HSA at pH 6.4.

B. Spray Drying

A dry powder of the DNA:Lipid vector formulation described above was produced by spray drying the aqueous mixture using a Buchi Laboratory Spray Dryer under the following conditions:

| | |
|---|---|
| Temperature of aqueous mixture | 2–8° C. |
| Inlet temperature | 120° C. |
| Feed rate | 3.8 mL/min |
| Outlet temperature | 71° C. |
| Atomizer coolant temperature | 2–8° C. |
| Cyclone coolant temperature | 2–8° C. |

Once the aqueous mixture was consumed, the outlet temperature was maintained at 65° C. for about 5 minutes by slowly decreasing the inlet temperature to provide a secondary drying.

C. Characterization

The following characterization of the dry, powder formulation described above was carried out using the methods described in Example I unless indicated otherwise.

The above 0.71% DNA:Lipid vector dry powder composition contained 93.97% glycine, and 5.32% HSA.

The particle size distribution of the composition was determined to be 2.0 µm MMD.

The delivered dose of the 97% heparin (HMW) powder was determined to be 64.0±1.0%.

The aerosol particle size distribution, was determined to be 2.4 μm MMAD, with 75% of the particles <5.0 μm in diameter.

Activity after spray drying was determined to be 160% of the expected value.

EXAMPLE XII

Adenoviral Vector Gene Formulation for Pulmonary Delivery

A. Formulation

Bulk pCMVP DNA:Adenovirus vector as described in U.S. application Ser. No. 08/422,563, filed Apr. 14, 1995, now U.S. Pat. No. 5,994,314 entitled COMPOSITIONS AND METHODS FOR NUCLEIC ACID DELIVERY TO THE LUNG, the disclosures of which are hereby incorporated by reference, was obtained from Genzyme Corporation, Cambridge, Mass. A 0.71% DNA: adenovirus vector formulation was achieved by combining $10^8$ PFU/mL DNA:Adenovirus vector per 1.0 mL deionized water with 6.1 mg/mL glycine (J. T. Baker), 2.5 mg/mL HSA, 1.9 mg/mL phosphate buffer at pH 7.4.

B. Spray Drying

| | |
|---|---|
| Temperature of aqueous mixture | 2–8° C. |
| Inlet temperature | 105° C. |
| Feed rate | 2.9 mL/min |
| Outlet temperature | 72° C. |
| Atomizer coolant temperature | 2–8° C. |
| Cyclone coolant temperature | 20° C. |

Once the aqueous mixture was consumed, the outlet temperature was maintained at 70° C. for about 10 minutes by slowly decreasing the inlet temperature to provide a secondary drying.

C. Characterization

The following characterization of the dry powder formulation described above was carried out using the methods described in Example I unless indicated otherwise.

The above DNA:adenovirous vector dry powder composition contained 58% glycine, and 24% HSA and 18% phosphate buffer.

The particle size distribution of the composition was determined to be 2.3 μm MMD.

The delivered dose of the 97% heparin (HMW) powder was determined to be 51.0±1.0%.

The aerosol particle size distribution, was determined to be 1.8 μm MMAD, with 80% of the particles <5.0 μm in diameter.

Activity after spray drying was determined to be 76% of the expected value.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. Biocompatible particles for delivery of a therapeutic, prophylactic or diagnostic agent to the pulmonary system comprising a therapeutic, prophylactic or diagnostic agent wherein the particles have a tap density of 0.34 g/cm$^3$ and the particles have an MMAD of 1 μm with 90% of the particles <5.0 μm in diameter wherein said agent is alpha-1-antitrypsin.

2. Biocompatible particles for delivery of a therapeutic, prophylactic or diagnostic agent to the pulmonary system comprising a therapeutic, prophylactic or diagnostic agent which is a protein; wherein the particles have a tap density of 0.34 g/cm$^3$ and the particles have a diameter of about 1.71 μm MMD and an MMAD of 1 μm with 90% of the particles <5.0 μm in diameter wherein said agent is alpha-1-antitrypsin.

* * * * *